United States Patent [19]

Pocknell

[11] Patent Number: 4,791,149
[45] Date of Patent: Dec. 13, 1988

[54] METHODS OF MAKING DRESSINGS

[75] Inventor: David Pocknell, Antibes, France

[73] Assignee: Dow Corning France S.A., Valbonne, France

[21] Appl. No.: 929,252

[22] Filed: Nov. 10, 1986

[30] Foreign Application Priority Data

Nov. 12, 1985 [FR] France ............................. 85 16655

[51] Int. Cl.$^4$ .............................................. C08L 6/00
[52] U.S. Cl. .................................... 523/111; 524/862; 529/31; 529/32; 529/15; 206/221; 222/145; 222/135
[58] Field of Search ................ 523/111; 528/31, 32, 528/15; 524/862; 206/221; 222/145, 135

[56] References Cited

U.S. PATENT DOCUMENTS

| | | | |
|---|---|---|---|
| 2,875,163 | 2/1959 | Berridge et al. | 260/2.5 |
| 3,923,705 | 12/1975 | Smith | 260/2.5 S |
| 4,157,426 | 6/1979 | Hatanaka et al. | 521/122 |
| 4,229,548 | 10/1980 | Sattlegger et al. | 521/110 |
| 4,439,416 | 3/1984 | Cordon | 424/47 |
| 4,547,529 | 10/1985 | Lee et al. | 521/122 |
| 4,550,125 | 10/1985 | Lee et al. | 521/117 |
| 4,555,529 | 11/1985 | Lee et al. | 521/124 |
| 4,608,396 | 8/1986 | Bauman et al. | 521/99 |
| 4,621,029 | 11/1986 | Kawaguchi | 428/447 |

FOREIGN PATENT DOCUMENTS

| | | |
|---|---|---|
| 0121342 | 10/1984 | European Pat. Off. |
| 2012999 | 3/1970 | France . |
| 2312527 | 12/1976 | France . |
| 0861448 | 2/1961 | United Kingdom . |
| 1492581 | 11/1977 | United Kingdom . |

OTHER PUBLICATIONS

U.S. Patent Application Ser. No. 928,939, filed 11/10/86, by David Pocknell, entitled "Organosiloxane Foams", Docket No. VN-1.
U.S. Patent Application Ser. No. 929,250, filed 11/10/86 by David Pocknell, entitled "Methods of Making Dressings", Docket No. VN-3A.
Derwent abstract for French patent 2,312,527.

Primary Examiner—Joseph L. Schofer
Assistant Examiner—Peter D. Mulcahy
Attorney, Agent, or Firm—Susan M. Cornwall

[57] ABSTRACT

The specification is directed to making noncellular dressings such as gelatinous wound dressings. According to the invention medical and surgical dressings are made by use of packages which may be held in the hand, and which contain the components of two part curable polysiloxane compositions in such a manner that the component may be mixed in predetermined proportions and dispensed therefrom under the influence of propellant gas. The method avoids the need for manual mixing of such compositions during production of dressings.

6 Claims, 1 Drawing Sheet

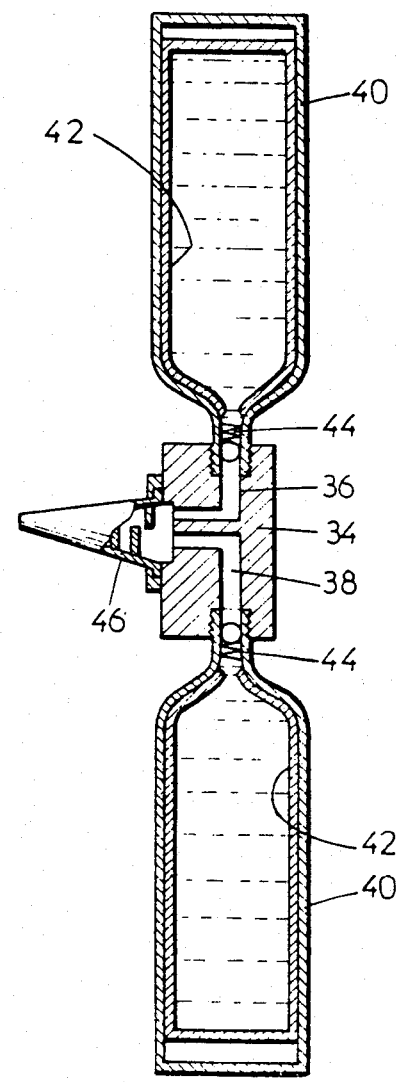

METHODS OF MAKING DRESSINGS

BACKGROUND OF THE INVENTION

This invention is concerned with making non-cellular dressings i.e. dressings for surgical or medical treatment of the human or animal body.

It has been proposed to employ two-part curable organosiloxane compositions for preparation of dressings. For example G.B. patent specification No. 1 492 581 describes dressings for open granulating wounds made by a process in which the two parts of a composition are mixed and then poured into an open wound where the composition cures to provide an elastomeric dressing. Compositions proposed for making such dressings have comprised poly(dimethylsiloxane) and finely divided filler base or "part A", and a catalyst part or "part B" comprising catalyst material for promoting room temperature curing and foaming of the composition according to the scheme $\equiv SiOH + HSi \equiv \rightarrow \equiv Si-O-Si \equiv + H_2$. By use of these compositions one may provide comfortable, non-adherent dressings conforming to the contours of the wound which are inter alia soft, resilient, permeable to air and somewhat absorbent.

Such a procedure for producing dressings leads to a variety of advantages related to improved patient comfort e.g. resulting from the non-adherent characteristics of the dressing and reduced care from nursing staff e.g. due to the increased possibility for the patient to remove the dressing to permit washing and/or disinfecting of the wound and dressing, followed by replacement of the dressing.

The correct use of two component compositions entails correct proportioning of the components and adequate mixing thereof. Adequate mixing of components of different viscosities can prove tedious when manual methods are used, but in general hand mixing of two part compositions or their component parts may be carried out by use of a suitable stirring implement, for example, a spatula. However, apart from the tedium involved, such mixing may lead to entrapment of air bubbles in the compositions. Particularly in those cases where more viscous compositions or faster curing compositions are used, these bubbles may become trapped in the composition as it cures. Entrapped bubbles in dressings produced render the dressings non-uniform and thus of variable quality. This is generally undesirable and in some cases may be wholly unacceptable. In addition, exposure of the composition to the environment during mixing to produce dressings is undesirable as it may be unhygienic in view of the possibility of contaminating the dressing as it is produced.

Apart from the desirability of mixing together the components without exposure to the atmosphere, those compositions which have been proposed for use in accordance with G.B. Pat. No. 1 492 581 tend to require separate mixing of the part A prior to admixture of the parts A and B. In the proposed compositions separation of the filler from the other components may occur.

Thus, the step of mixing the part A of the composition just prior to use is a critical step. When this step, or the proportioning of ingredients is not carried out adequately or at all (as may happen in practice), poor quality dressings result. It is troublesome to rectify improper mixing of such compositions because very often the fact of improper mixing is not recognized until after the supposedly curing composition has been applied to its allotted position. After recognition of failure to provide a suitably cured mass it becomes desirable to remove the defective material, clean up the site and to achieve the desired result by correct application or by some other practice. Such remedial operations are troublesome and inconvenient and are especially so in those cases where the product is used to provide a treatment for an open wound for example on the human body.

It is common practice to package materials in so-called aerosol form, particularly for surface coating applications. Materials which are usually packaged in this way consist primarily of liquids or solutions of comparatively low viscosity and which essentially do not require mixing with another ingredient prior to ejection from the package. Proposals have been made to extend the use of aerosol type packaging to curable two-part compositions. For example in G.B. specification No. 861 448 there is described and claimed a package comprising a pressure tight container having a closeable outlet orifice and containing a polymerizable material of such a nature that it will convert at a temperature below approximately 150° F. (b 65° C.) rapidly and completely to an organic polymer only when released from said outlet orifice, and a propellant that is gaseous at room temperature and pressure, said propellant being present in a sufficient quantity and being capable of exerting a sufficient pressure within the container to expel said polymerizable material through said orifice. In a preferred form of construction, an agent for activating polymerization is maintained with a volatile propellant physically separated from the polymerizable material in a compartment from which it may be expelled through an orifice into a mixing chamber wherein said polymerizable material and said activator are blended under reduced pressure prior to being expelled to the atmosphere.

The applicant has found it impossible satisfactorily to package certain curable polysiloxane compositions using known aerosol type packages. There exists a particular problem of packaging filled materials which have a consistency which is thicker than the liquid polysiloxane fluids and these materials are among those which are particularly beneficial for the production of dressings.

SUMMARY OF THE INVENTION

It is one of the objects of the present invention to provide an improved method of making a non-cellular dressing.

The Applicant has now found that a dressing, i.e., a mass conforming to the contours of a wound or body and which is inter alia, non-adherent, permeable to air and preferably resilient and somewhat absorbent, may be readily produced by use of a two compartment package containing selected two component polysiloxane compositions.

The invention provides in one of its aspects, a method of making a medical dressing comprising the steps of (A) procuring a package containing a room temperature curable polysiloxane composition comprising two component parts comprising ingredients which together provide an organosilicon polymer including siloxane units having an alkenyl group having 2 to 4 carbon atoms inclusive, an organosilicon polymer including siloxane units having a silicon-bonded hydrogen atom and a catalyst, the organosilicon polymers being such that they are capable of chemical reaction at room temperature when mixed in the presence of the catalyst to provide a non-cellular polysiloxane mass, said package comprising two separate compartments within a container, one compartment for each component of the composition, each compartment of which contains, within a membrane, a component part of the composition where the ingredients present in each such component do not react with each other, there being a propellant located between the membrane and the container whereby the membrane may be caused by the propellant gas to expel the component when required, the package being so constructed and arranged that it may operate to mix predetermined proportions of the components in the absence of air and to dispense the mixed composition from the package, (B) operating the package to bring about mixing of the components in said predetermined proportions and (C) dispensing the mixed composition from the package to provide said dressing in a desired shape.

Compositions suitable for use in a method according to the invention preferably are capable upon admixture of their component parts of becoming cured in a short time at room temperature to provide a polysiloxane mass. For many purposes, a composition curable within a few minutes at temperatures in the range of about 15° C. to 30° C. without application of heat is desirable. Such compositions may comprise parts A and B of similar or different viscosities and providing components of the curable composition which are interactive or catalytic one with the other and thus stored separated to avoid premature cure.

BRIEF DESCRIPTION OF THE DRAWING

The above and other objects, features and advantages of the present invention will become apparent to those skilled in the art upon an examination of the following description and drawing.

FIG. 1 is a schematic diagram showing a "can-on-can" type of package.

DETAILED DESCRIPTION OF THE INVENTION

Suitable organosilicon polymers having a silicon-bonded hydrogen atom for use in the invention include alkylhydrogen polysiloxanes having units according to the general formula $$R_pH_qSiO_{\frac{(4-(p+q))}{2}}$$

in which each R represents a lower alkyl group of from 1 to 6 carbon atoms or phenyl radical, e.g., a methyl radical, p is 0, 1 or 2, q is 1 or 2 and the sum of p and q is 1, 2 or 3. The alkylhydrogen polysiloxanes may also comprise units $$R_nSiO_{\frac{(4-n)}{2}}$$

in which R is as defined above and n has the value 1, 2 or 3.

Curing reactions of the preferred compositions are dependent on presence of appropriate proportions of the interactive silicon-bonded substituents and the alkylhydrogen polysiloxane may be selected accordingly. I prefer that each R represents a methyl group. Preferably, terminal groups of the alkylhydrogen polysiloxane are $R_3SiO_{\frac{1}{2}}$ groups where each R represents a methyl group. Suitable alkylhydrogen polysiloxanes include those comprising predominantly MeHSiO units with or without the presence of Me$_2$SiO and having viscosities of the order of from about 0.001 to about 0.1 Pascal-seconds ("Pa.s"), preferably 0.001 to 0.05 Pa.s at 25° C.

Suitable organosilicon polymers having alkenyl groups having 2 to 4 carbon atoms inclusive include alkenyl polysiloxanes having units according to the general formula $$R_m(Q)SiO_{\frac{(3-m)}{2}}$$

in which each Q represents an alkenyl group having 2 to 4 carbon atoms, inclusive, for example, a —CH=CH$_2$ or a —CH$_2$CH=CH$_2$ group, each R represents a lower alkyl radical of from 1 to 6 inclusive carbon atoms or phenyl radical, e.g., a methyl radical and m is 1 to 2. These polysiloxanes also comprise units $$R_nSiO_{\frac{(4-n)}{2}}$$

in which R is as defined above and n is 1, 2 or 3. These materials are preferably liquids and are chosen so that their functionality is appropriate in relation to the degree of chain extension and crosslinking required during curing of the composition. I prefer to employ polysiloxanes which are essentially difunctional i.e. α,ω-di-alkenyl polysiloxanes. Suitable materials include dimethylvinyl end-blocked polysiloxanes having viscosities up to about 85 Pa.s, preferably less than 10 Pa.s and more preferably less than 2.5 Pa.s at 25° C. Other suitable materials include phenylmethylvinyl end-blocked polydimethylsiloxanes, for example, those having viscosities at 25° C. of 0.25 to 10 Pa.s.

In the preferred materials, the R groups are predominantly methyl radicals. In preferred compositions according to the invention, the preferred alkenyl functional polysiloxanes thus provided polysiloxane chains of significant length and this is desirable in view of flexibility and elastomeric properties required of the product resulting from curing of the composition.

If desired the composition for use in the invention may contain fillers. Fillers suitable for use in the invention preferably comprise hydrophobic materials which may be prepared by treatment of finely divided silica with organosilanes, organosiloxanes, organosilazanes or alkylsilanols. Suitable organosilanes include those represented by the general formula $(R)_aSi(X)_b$ in which each R represents a lower alkyl or aryl radical for example a methyl radical, each X represents a hydroxyl radical or halogen atom, for example, Cl or Br, and each of a and b is 1, 2 or 3 and a+b=4. Examples of such materials include trimethyl monochlorosilane, dimethyl dichlorosilane and trimethyl monohydroxysilane. The hydroxysilanes may be produced for example by hydrolysis of appropriate alkyl disilazanes; for example one preferred filler material is a reaction product derived from silica and hexamethyldisilazane in presence of water. Suitable filler materials have a surface area between about 50 and about 300 m$^2$/g and preferred materials have a surface area between about 100 and about 250 m$^2$/g. These hydrophobic fillers may be prepared, for example, by addition of the silica and alkyldisilazane to other ingredients of the composition during preparation of the composition or, more preferably, the hydrophobic filler is prepared in a separate operation prior to addition to the other ingredients of the composition.

If desired, untreated finely divided filler materials may also be included in the composition in amounts which do not lead to undesirable settlement of the filler in the composition during storage prior to curing. Suitable fillers include metal oxides, clays and silicas.

The organosilicon polymers are such that they are capable of chemical reaction at room temperature when mixed in presence of the catalyst. The catalyst may be any of those conventionally employed to promote the hydrosilylation reaction and may be for example a platinum catalyst in any of the known forms, ranging from platinum as deposited on carriers such as silica gel or powdered charcoal, to platinic chloride, salts of platinum and chloroplatinic acid. A preferred form of platinum is the chloroplatinic acid either as the commonly obtainable hexahydrate or the anhydrous form, on account of its easy dispersibility in organosilicon systems and its non-effect on color of the mixture. Another preferred platinum catalyst is a chloroplatinic acid catalyst complex as prepared by the method described in U.S. Pat. No. 3,419,593, where chloroplatinic acid hexahydrate is mixed with symmetrical divinyltetramethyldisiloxane to provide the complex. Another similar complex is one prepared from the chloroplatinic acid hexahydrate, symmetrical divinyltetramethyldisiloxane, symmetrical tetramethyldisiloxane and alcohol solvent. Other suitable platinum compounds include $PtCl_2\{P(CH_2CH_2CH_3)_3\}_2$, platinum bromides, a complex of platinous halide and an olefin such as ethylene, propylene, butylene cyclohexene and styrene, $Pt(CH_3CN)_2Cl_2$, $\{Pt(CH_2CN)_2(CH_3)_4\}Cl_2$, $Pt(NH_3)_2Cl_2$, $K\{PtCl_3CH_2CH_2CH_2OH\}$, $PtBr_2(C_2H_4)_2$, $K\{PtBr_3(C_2H_4)\}$, $PtCl_2(C_2H_4)$, $(CH_3)_2C=CH_2.PtCl_2$, $H_2Pt(CN)_4.5H_2O$, $H\{PtCl_3(CH_2CN)\}$, $Pt(NH_3)_2(CNS)_2$, $PtCl_2.PCl_3$, $\{Pt(NH_3)_4\}.\{PtCl_4\}$, $PtCl_2\{P(CH_2CH_3)_3\}_2$, $\{PtCl_2\}.P(OCH_2CH_3)_2$, $Pt(OOCH_2SCH_2CH_3)_2$, $Pt(CN)_3$, $(CH_3)_4Pt$, $(CH_3)_3Pt-Pt(CH_3)_3$, $(CH_3)_3Pt(CH_2COCH=C(OH)CH_3)$, $PtCl_2CO$ and $PtBr_2CO$.

Higher functional materials may be included in the composition as crosslinking agents. Suitable organosilicon crosslinking agents include materials having, per molecule, three or more functional groups which are reactive with functional groups present on other components of the mixture, for example, a copolymer of dimethyl and polymethylhydrogen siloxanes having at least three $\equiv$SiH groups per molecule.

Examples of some of the materials described above can be found in U.K. Patent Specification No. 1 522 637 and its corresponding U.S. Pat. No. 3,923,705. Others will be evident to those skilled in the art based on the descriptions provided herein.

Compositions for use in the invention which are intended for preparation of, the preferred, somewhat resilient gelatinous dressings may conveniently be ones in which chain extension and/or crosslinking reactions involve primarily vinyl addition reactions and thus do not have the ability to provide expansion provoking amounts of evolved hydrogen. Quantities of materials used may be varied within wide ranges depending on the materials used and on the properties required of the dressing. Preferred materials may be employed for example to provide elastomeric dressings in amounts as follows:

| Materials | Parts by Weight | |
|---|---|---|
| | Preferred Amounts | More Preferred Amounts |
| α,ω-(dimethylvinyl) polysiloxane of viscosity less than 85 Pa.s | 100 | 100 |
| α,ω-di(methylphenylvinyl) polysiloxane of viscosity from 0.25 to 10 Pa.s | 0–40 | 30–40 |
| Copolymer of dimethyl and polymethylhydrogen siloxanes | 0.5–15 | 10–15 |
| Filler | 0–50 | 40–48 |
| Platinum catalyst | 0.05–0.2 | 0.08–0.16 |

Packages for use in the invention have two compartments or chambers from which chambers the components may be expelled by the action of propellant gas on a membrane within the chamber. The propellant gas is located between the membrane and a surface of the chamber, so that it is not expelled from the chamber with the composition.

Suitable propellants include hydrocarbons, for example, methane, ethylene, ethane, propane, neopentane and the many halogenated hydrocarbons especially the fluorinated hydrocarbons, for example methyl fluoride, trifluoromethane, monochlorodifluoromethane and dichlorodifluoromethane.

The chambers of the package may be arranged one within the other or one adjacent the other and the construction and arrangement is such that the package may be operated so that curing composition is dispensed from the package with its components mixed in predetermined proportions. Preferably the package has a mixer nozzle through which the component parts of the composition may be passed to mix them together. The chambers may be arranged to dispense single, or more preferably multiple, doses per package as desired. Plastics, metal or glass, moisture proof chambers are preferably used.

A package for use in the invention may comprise, for example, two adjacent compartments each containing a component part of the composition. One or each component part may comprise organopolysiloxane and hydrophobic filler. These compartments may be arranged and adapted to discharge their contents in desired proportions via a manifold to a mixing nozzle when required, seriatim until the compartments have been emptied.

Packages for use in the invention preferably are designed for simple manual operation and may contain sufficient composition for use in those situations where comparatively small quantities of composition are likely to be required at any particular time. Advantages of the invention are particularly beneficial when it is important to ensure suitable admixture of the parts of the composition with minimal operator attention, and where contamination of the composition by air entrapment and/or otherwise is to be avoided.

By use of the invention one can avoid the need for hand mixing of dressing compositions and one can produce surgical and medical dressings which are non-adherent to wounds, permeable to air, slightly absorbent and slightly permeable to moisture and which may have bacteriostatic properties. The compositions may be cast into a desired shape by dispensing the mixture onto a suitably shaped substrate. In those cases where a dressing conforming to the shape of a particular wound or body surface is required, it is most convenient to dispense the mixture directly onto the wound or body surface and to allow the composition to cure in situ to form the dressing. If desired, stiffening or supporting materials, for example, one or more gauze layers or a sleeve, may be introduced into the mass of mixed composition before completion of curing of the composition to increase the stiffness or durability of the dressing.

In order that the invention may be more fully understood, there now follows a description of one illustrative example method of making dressings provided by the invention.

The curable composition hereinafter referred to comprises two components and is capable of curing at room temperature of 18.5° C.±3° C. when the components are mixed to provide a wound dressing.

Example compositions 1 and 2 provided Parts A and B, respectively, for mutual admixture to provide a curing composition curing at about 18° C. within 5 minutes and suitable for formation of gelatinous burn dressings. The compositions comprised the following materials in the amounts by weight shown:

| Material | Example Composition | |
|---|---|---|
| | 1 | 2 |
| $\alpha,\omega$-alkenyl polysiloxane-fluid-1 | 75 | 75 |
| $\alpha,\omega$-alkenyl polysiloxane fluid-2 | 25 | 25 |
| Platinum catalyst | — | 0.55 |
| Alkylhydrogen siloxane 1 | 6 | — |
| Polydimethylsiloxane fluid 1 | 20 | 20 |

The $\alpha,\omega$-alkenyl polysiloxane fluid-1 used was a high molecular weight polydimethylsiloxane polymer with dimethyl vinyl end-blocking having a viscosity of 1.8 to 2.4 Pa.s at 25° C.

The $\alpha,\omega$-alkenyl polysiloxane fluid-2 used was a low molecular weight polydimethylsiloxane with dimethylvinyl end-blocking and a viscosity of 0.3 to 0.5 Pa.s at 25° C.

The alkylhydrogen siloxane 1 used was a copolymer of polydimethyl and polymethylhydrogen siloxanes having an SiH content (as % H) of about 0.69 to 0.83 and a viscosity of 0.004 to 0.006 Pa.s at 25° C.

The polydimethylsiloxane fluid 1 was a trimethyl endblocked material of viscosity of 0.25 to 0.5 Pa.s at 25° C.

EXAMPLE 1

Equal 100 g volumes of example composition 1 and 2 were packaged in a "can-to-can" package of the type shown in FIG. 1. Each can (40) was provided by a metal container and had an elastic membrane lining (42) secured adjacent an outlet of the container. Each container contained, between its container wall and the membrane lining (42), 10 g of FREON ®12 fluorinated hydrocarbon ("FREON" is a trademark of E. I. duPont de Nemours and Company of Wilmington, Del.) which was intended subsequently to provide propellant gas pressure destined to act upon the membrane to dispense the composition. Each container was closed by means of a one-way valve (44) and the one-way valves were secured in ports (36, 38) of a manifold block (34). The ports communicated with a mixer nozzle (46) for mixing the two compositions. The ports were arranged so that equal volumes of the two Compositions 1 and 2 were delivered under the influence of the propellant gases to the mixer nozzle upon opening of the one-way valves. The Compositions 1 and 2 were thus dispensed in predetermined volumes and mixed together upon operation of the package.

Composition dispensed from the nozzle was in the form of a bead which cured within 5 minutes to a uniform resilient non-foamed product. The mixed, during composition was dispensed onto a patient to provide a gelatinous burn dressing.

Other modifications and variations in the method of the present invention will become apparent to those skilled in the art from an examination of the above specification and drawing. Therefore, other variations and modifications of the present invention may be made which fall within the scope of the following claims even though they were not specifically discussed above.

That which is claimed is:

1. A method of making a medical dressing comprising the steps of
   (A) procuring a package containing a room temperature curable polysiloxane composition consisting essentially of two component parts comprising ingredients which together provide an organosilicon polymer including siloxane units having an alkenyl group having 2 to 4 carbon atoms inclusive, an organosilicon polymer including siloxane units having a silicon-bonded hydrogen atom and a catalyst, the organosilicon polymers being such that they are capable of chemical reaction at room temperature when mixed in the presence of the catalyst to provide a non-cellular polysiloxane mass, said package comprising two separate compartments within a container, one compartment for each component of the composition, each compartment, within a membrane, consists essentially of a component part of the composition where the ingredients present in each such component do not react with each other, there being a propellant located between the membrane and the container whereby the membrane may be caused by the propellant gas to expel the component when required, the package being so constructed and arranged that it may operate to mix predetermined proportions of the components in the absence of air and to dispense the mixed composition from the package,
   (B) operating the package to bring about mixing of the components in said predetermined proportions and
   (C) dispensing the mixed composition from the package to provide said dressing in a desired shape.

2. A method according to claim 1 wherein said composition further comprises a finely divided hydrophobic filler.

3. A method according to claim 2 wherein said filler material is a product of the treatment of finely divided silica with hexamethyl disilazane in presence of water and has a surface area between about 100 and 250 m²/g.

4. A method according to claim 2 wherein said package is provided with a mixer nozzle through which the predetermined proportions of the components are expelled.

5. A method according to claim 2 wherein the curable composition consists essentially of 100 parts by weight of an $\alpha,\omega$-di-alkenyl polysiloxane composed of $R_2(Q)SiO_{\frac{1}{2}}$ endblocking units and $R_2SiO$ units having a viscosity of less than 85 Pa.s at 25° C., 0–40 parts by weight of a $\alpha,\omega$-di-alkenyl polysiloxane composed of $R_2(Q)SiO_{\frac{1}{2}}$ endblocking units and $R_2SiO$ units having a viscosity of from 0.25 to 10 Pa.s at 25° C., 0.5 to 15 parts by weight of a copolymer of dimethylsiloxane units and methylhydrogen siloxane units, no more than 50 parts by weight of finely divided hydrophobic filler and 0.05 to 0.2 parts by weight of a platinum catalyst where each Q is an alkenyl group having 2 to 4 inclusive carbon atoms and each R is an alkyl group of from 1 to 6 inclusive carbon atoms or a phenyl group.

6. A method according to claim 2 wherein the curable composition consists essentially of 100 parts by weight of an α,ω-di-alkenyl polysiloxane composed of $R_2(Q)SiO_{\frac{1}{2}}$ endblocking units and $R_2SiO$ units having a viscosity of less than 2.5 Pa.s at 25° C., 30–40 parts by weight of a α,ω-di-alkenyl polysiloxane composed of $R_2(Q)SiO_{\frac{1}{2}}$ endblocking units and $R_2SiO$ units having a viscosity of from 0.25 to 10 Pa.s at 25° C., 10 to 15 parts by weight of a copolymer of dimethylsiloxane units and methylhydrogen siloxane units, 40 to 48 parts by weight of finely divided hydrophobic filler and 0.08 to 0.16 parts by weight of a platinum catalyst where each Q is an vinyl group and each R is a methyl group.

* * * * *